United States Patent [19]

Sprouse et al.

[11] Patent Number: 4,536,603
[45] Date of Patent: Aug. 20, 1985

[54] PRODUCTION OF ACETYLENE FROM COAL BY CONTACT WITH A COMBUSTION GAS

[75] Inventors: Kenneth M. Sprouse, Northridge; Merlin D. Schuman, Canoga Park; L. Paul Combs, Woodland Hills, all of Calif.

[73] Assignee: Rockwell International Corporation, El Segundo, Calif.

[21] Appl. No.: 564,643

[22] Filed: Dec. 22, 1983

[51] Int. Cl.³ .................... C10B 49/02; C10B 49/08; C10G 1/00
[52] U.S. Cl. .................... 585/539; 585/534; 585/537; 208/8 R
[58] Field of Search ............... 585/539, 534, 537, 538, 585/943; 208/8 R; 48/210

[56] References Cited

U.S. PATENT DOCUMENTS

| | | | |
|---|---|---|---|
| 2,343,866 | 3/1944 | Hincke | 585/537 |
| 2,767,233 | 10/1956 | Mullen, II et al. | 585/541 |
| 2,790,838 | 4/1957 | Schrader | 585/539 |
| 2,912,475 | 11/1959 | Krause et al. | 585/539 |
| 3,178,488 | 4/1965 | Akin | 585/539 |
| 3,384,467 | 5/1968 | Ammann et al. | 48/65 |
| 3,692,862 | 9/1972 | Staud et al. | 585/539 |
| 3,842,138 | 10/1974 | Chahvekilian et al. | 585/501 |
| 3,997,423 | 12/1976 | Greene | 208/8 R |
| 4,166,830 | 9/1979 | Guth et al. | 585/539 |
| 4,206,032 | 6/1980 | Friedman et al. | 208/8 R |
| 4,243,509 | 1/1981 | Sinor | 208/8 R |
| 4,256,565 | 3/1981 | Friedman et al. | 208/129 |
| 4,336,125 | 6/1982 | Weil et al. | 208/8 R |
| 4,358,629 | 11/1982 | Kim | 585/538 |
| 4,412,908 | 11/1983 | Yamashita et al. | 208/107 |
| 4,487,683 | 12/1984 | Bozzuto | 208/8 R |

FOREIGN PATENT DOCUMENTS

| | | | |
|---|---|---|---|
| 1286111 | 2/1961 | France | 585/539 |
| 1555656 | 1/1969 | France | |
| 1068552 | 5/1967 | United Kingdom | 585/539 |
| 2101151 | 1/1983 | United Kingdom | |

Primary Examiner—D. E. Gantz
Assistant Examiner—Lance Johnson
Attorney, Agent, or Firm—H. Fredrick Hamann; Harry B. Field

[57] ABSTRACT

A process wherein coal is reacted with a hot gas stream to produce acetylene. The process comprises the sequential steps of reacting a fuel, oxygen and steam under controlled conditions of temperature to produce a hot gas stream principally comprising hydrogen, carbon monoxide and steam along with minor amounts of carbon dioxide, and essentially free of O, OH and $O_2$. The hot gas stream is accelerated to a high velocity and impinged upon a stream of particulate bituminous or subbituminous coal and thereafter the mixture of hot gas and coal is decelerated to a velocity of from about 150 to 300 feet per second. The amounts of the streams of particulate coal and hot gas are controlled to produce in the reaction zone a pressure in the range of from about 10 to 100 psia and a temperature of from about 1800° to 3000° F. The mixture of coal and hot gas is maintained at that pressure and temperature for a time of from about 2 to 30 milliseconds to produce a product stream including char and acetylene. The temperature of the product stream is then reduced to less than about 900° F. in a time of less than about 2 milliseconds to substantially arrest any further reactions and the acetylene is recovered therefrom. The char is recovered and used as at least a part of the fuel used to produce hot gas.

25 Claims, 1 Drawing Figure

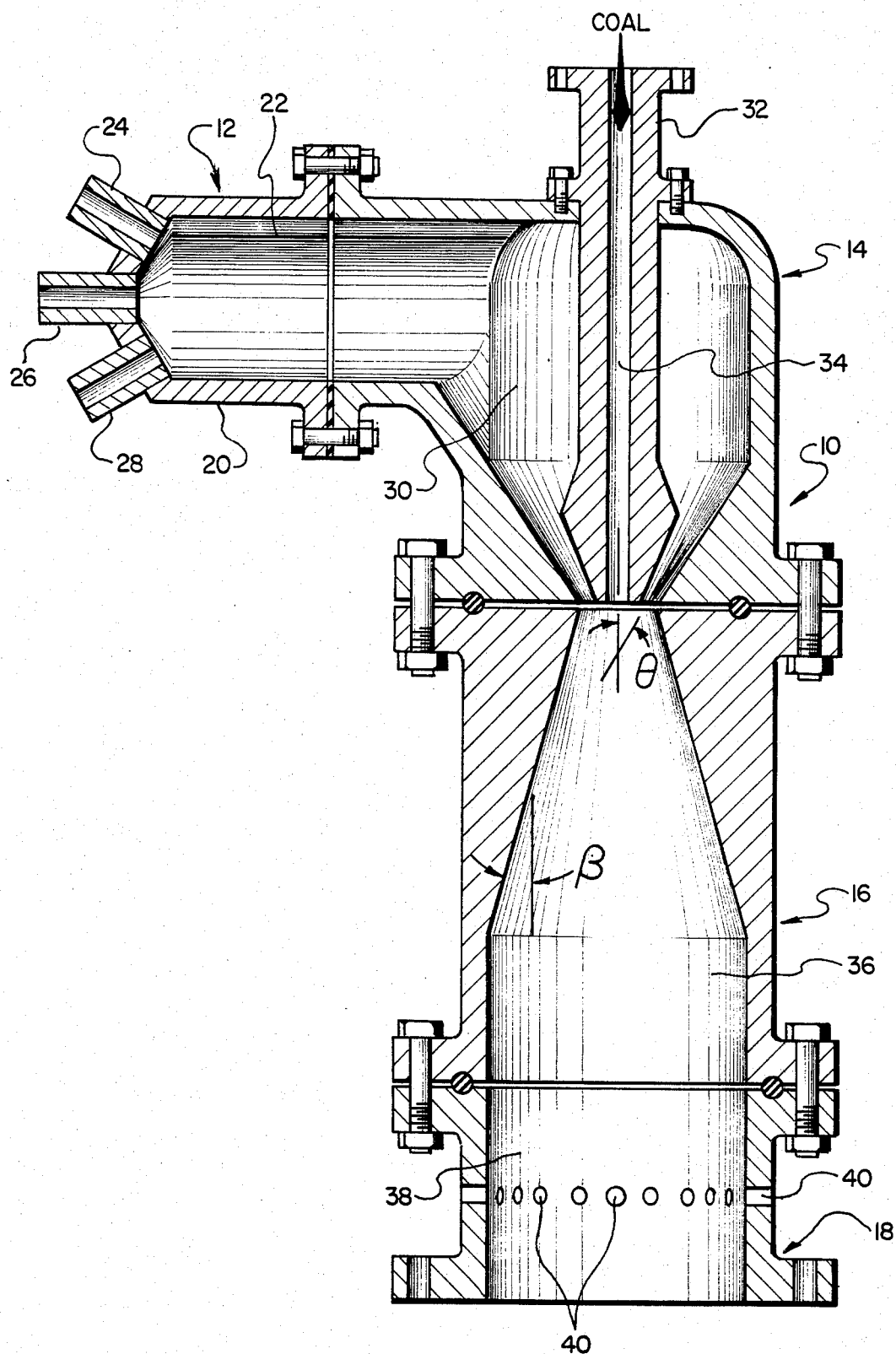

PRODUCTION OF ACETYLENE FROM COAL BY CONTACT WITH A COMBUSTION GAS

FIELD OF INVENTION

The present invention broadly relates to the treatment of coal with a hot gas stream to produce acetylene. It particularly relates to a process which includes the rapid heating, mixing and short residence time treatment of coal with a hot gas stream principally comprising hydrogen, carbon monoxide and steam to produce enhanced yields of acetylene.

PRIOR ART

It is well known that hydrocarbons may be converted to olefins by thermal pyrolysis, generally referred to as steam cracking. In most such prior art processes, the steam is used as the heat transfer fluid to convert gaseous hydrocarbon feedstocks to olefins. In U.S. Pat. No. 2,767,233, there is disclosed a process for the thermal transformation of hydrocarbons. The patent broadly teaches reacting a hydrocarbon with a hot gas stream comprising the combustion products of a fuel and a gaseous oxidant. The patent specifically teaches the introduction of a hydrocarbon reactant into hot combustion gases in an elongated chamber in at least a portion of which the reactant and gases flow at a high velocity of at least 1000 feet per second, and thereafter quickly cooling the reaction gases and recovering the reaction products therefrom. The specific hydrocarbon reactants disclosed are pentane, kerosene, propane and methane for the production of acetylene. The patent also discloses the production of ethylene and synthesis gas from pentane and methane, respectively. In all of the examples, however, it is noted that the feedstock is either a gas or a light, readily vaporizable hydrocarbon. Thus, the patent contains no teaching or suggestion of a method of producing acetylene from a solid feedstock, such as coal.

U.S. Pat. No. 2,912,475 relates to the manufacture of low molecular weight unsaturated hydrocarbons (olefins). The patent discloses a process wherein a stream of hot combustion gases is mixed with a secondary lower temperature gas stream containing steam or hydrogen and which is free of any molecular oxygen. Thereafter, the combined stream is passed through a restricted opening into a reaction zone wherein the gas stream is contacted with a hydrocarbon to pyrolyze the hydrocarbon and form the desired olefin product. The patent broadly suggests that heavy hydrocarbons could be used as the feedstock; however, the examples are all restricted to the prior art lighter hydrocarbons. This patent also is deficient in that it does not teach a process for producing high yields of acetylene from a solid feedstock, such as coal.

More recently, in U.S. Pat. No. 3,842,138, there is disclosed a method of cracking hydrocarbons under hydrogen pressure for the production of olefins. In accordance with the teaching of this patent, the process is conducted in a heated reactor under superatmospheric pressure in the presence of hydrogen in temperatures higher than about 625° C. and with a residence time within the reaction section of less than about 0.5 second. This patent discloses the use of a variety of light hydrocarbon feedstocks suitable for use in the described process. However, the patent clearly teaches that aromatics are not desirable in substantial quantity in the feedstock and states that since, ". . . their nuclei have great thermal stability and are relatively refractory to the action of hydrogen under the operating conditions, their presence in the feed is only tolerated, . . . " Thus, this patent recognizes the problems inherent with thermal cracking of complex feedstocks, such as coal, but fails to offer any teaching or suggestion as to how to overcome these difficulties.

U.S. Pat. No. 3,384,467 describes a process for thermally decomposing a carbonaceous material, coal in particular, into lower molecular weight hydrocarbons such as ethylene and acetylene. The process disclosed therein utilizes an electric arc furnace having at least two electrodes wherein coal is used to form at least a portion of one of the electrodes. While processes which use an electric arc for heating have reportedly produced significant yields of olefins and acetylene, it also must be appreciated that the high electrical power requirements are such that the processes are commercially uneconomical at this time.

In U.S. Pat. No. 4,206,032 there is described a method for the hydrogenation of a carbonaceous material such as coal. In accordance with the method disclosed therein, the coal is reacted with a heated gas principally comprising hydrogen and containing a minor amount of water vapor. The reaction takes place in an entrained flow reactor. The patent broadly describes the production of liquid and gaseous hydrocarbon products. It does not, however, provide specific guidance for the production of acetylene. In addition, the process described therein would require a source of substantially pure hydrogen which would add considerably to the cost of the process.

U.S. Pat. No. 4,256,565 describes a method of producing olefins from hydrocarbons. In accordance with the method described therein a hot gas stream which comprises a major amount of hydrogen and a minor amount of water vapor is impinged upon a stream of a hydrocarbon which is heated to a temperature in excess of its melting point but below the temperature at which any substantial coke or tar forms. Clearly, this patent does not teach a method which would be applicable to the treatment of a nonmeltable, solid particulate material such as coal.

A recent United Kingdom patent application G.B. Ser. No. 2,101,151A describes a method for the gasification and production of acetylene from coal. In accordance with the method disclosed therein oxygen and hydrogen are separately preheated to at least 1400° K. and thereafter reacted to raise the total temperature of the combustion products to above 2000° K. to convert coal into volatiles and char. The volatiles are reacted with an excess of hydrogen at temperatures in excess of 1400° K. to produce acetylene. An obvious economic disadvantage of this process is the necessity of a source of sufficient oxygen and hydrogen for the reactions described.

From the foregoing discussion, it is seen that most of the prior art conversion techniques generally require the use of a gaseous or liquid hydrocarbon feedstock for the production of acetylene. Further, those which do not, have yet to be developed to the point where they are economically feasible. Clearly, in view of the diminishing supply of light feedstocks and their increasing cost it would be beneficial if there were a process for the production of acetylene from coal. This is particularly true in view of the availability of large domestic supplies of coal.

SUMMARY OF THE INVENTION

The present invention provides a commercially viable process for producing substantial yields of acetylene from coal. In accordance with the process, a fuel, oxygen and steam are introduced into a hot gas generation zone, the oxygen being introduced in an amount less than the stoichiometric amount required to react with all of the fuel. Generally, the oxygen is introduced into the hot gas generation zone in an amount to provide an equivalence ratio within the range of from about 1.0 to 4.0, and preferably about 2.0. The fuel, oxygen and steam are reacted within the hot gas generation zone at a superatmospheric pressure and a temperature within the range of from about 3000° to 4500° F. (1920° to 2760° K.) to produce a hot gas stream principally comprising hydrogen, carbon monoxide and steam along with minor amounts of carbon dioxide. The temperature within the hot gas generation zone is controlled such that the hot gas stream produced is essentially free of O, OH, and $O_2$. By essentially free, it is meant that the total of all of these latter three constituents amounts to less than about 0.2 volume percent of the total gas stream produced.

The hot gas is accelerated to a velocity within the range of from about 500 to 4000 feet per second (150 to 1220 meters per second) by passing it through a restricted opening, such as a nozzle, prior to introducing it into a coal reaction zone. Also introduced into the coal reaction zone is a stream of particulate coal having a median particle size less than about 100 microns and preferably less than about 75 microns. It is an essential element of the present invention that the coal be selected from the group consisting of bituminous and subbituminous coals, as only these coals will provide the desired yields of acetylene.

The particulate coal and hot gas stream are impinged upon one another to cause intimate mixing and reaction of the stream of particulate coal with the hot gas stream. The two mix to form an entrained flow of particulate coal in the hot gas stream which is decelerated to a velocity of from about 150 to 300 feet per second (46 to 92 meters per second). The amount of particulate coal and the amount of hot gas introduced into the reaction zone are controlled to produce in the reaction zone a pressure in the range of from about 10 to 100 psia (0.7 to 6.8 atm.) and a temperature of from about 1800° to 3000° F. (1260° to 1920° K.). The mixture of coal and hot gas are maintained at that pressure and temperature for a time of from about 2 to 30 milliseconds to produce a product stream entrained in the hot gas.

The product stream comprises enhanced yields of acetylene along with other reaction products and char. The product stream is rapidly quenched to reduce the temperature to less than about 900° F. (750° K.) in a time of less than about 2 milliseconds to substantially arrest any further reactions. Thereafter, the acetylene and char are separately recovered and, in the preferred embodiment, the char is utilized as a source of at least a part of the fuel introduced into the hot gas generation zone.

In accordance with the present invention, it is contemplated that the char could be introduced directly into the hot gas generator and comprise the sole source of fuel or only a portion of the fuel. Alternatively, of course, the char could be gasified in a separate reactor and the combustible gaseous products therefrom introduced into the hot gas generation zone after separation of any mineral matter therefrom.

BRIEF DESCRIPTION OF THE DRAWING

The sole FIGURE is a schematic illustration of an apparatus for practicing the process of the present invention.

DESCRIPTION OF PREFERRED EMBODIMENT

Referring to the drawing, therein is depicted a schematic of a reactor apparatus 10 for practicing the process of the present invention. Reactor apparatus 10 comprises a hot gas generator assembly 12, a reactant injector assembly 14, a reaction chamber 16 and a quench chamber 18. Hot gas generator assembly 12 comprises a housing 20 defining a hot gas generation zone 22. Housing 20 is provided with inlets 24, 26 and 28 for the introduction of steam, oxygen and a fuel, respectively. As depicted, hot gas generation zone 22 of housing 20 is in flow communication with an interior zone 30 of reactant injector assembly 14. Reactant injector assembly 14 also includes a coal injector tube 32. Coal injector tube 32 has a passageway 34 for the passage of coal therethrough. Passageway 34 and interior zone 30 are in flow communication with a reaction zone 36 which is located within reaction chamber 16. Reaction zone 36 is in turn in fluid communication with a quench zone 38 defined by quench chamber 18. A plurality of apertures or openings 40 is provided about quench zone 38 for the introduction therein of a cooling fluid which typically will be provided by a manifold, not shown.

In the operation of reactor apparatus 10, a fuel, oxygen and steam are introduced into gas generator assembly 12 through inlets 24, 26 and 28. Obviously, the fuel, oxygen and steam need not be introduced separately as depicted for illustrative purposes. If desired, they could be combined such that only two inlets were required or even a single inlet for the three. A key feature of the invention is not the manner in which they are introduced but rather the composition of the hot gas produced in gas generator assembly 12.

Io obtain the desired hot gas composition, it is essential of course that the oxygen be introduced in an amount less than that required to react with all of the fuel. Generally, the equivalence ratio in hot gas generation zone 22 will be in the range of from about 1.0 to 4.0, and preferably is about 2.0. The fuel, oxygen and steam are reacted at a superatmospheric pressure and a temperature within the range of from about 3000° to 4500° F. (1920° to 2760° K.) to produce the desired hot gas stream principally comprising hydrogen, carbon monoxide and steam, along with minor amounts of carbon dioxide. The pressure within hot gas generation zone 22 will generally be within the range of from about 20 to 200 psia (1.4 to 13.6 atm).

The temperature within hot gas generation zone 22 is controlled such that the hot gas stream produced is essentially free of O, OH and $O_2$. Generally, this is accomplished by maintaining the temperature within a preferred range of from about 3000° to 3500° F. (1920° to 2200° K.). If the temperature is too low then obviously an excessive amount of gas will be required to heat the coal to a desired reaction temperature. Conversely, if the temperature of the hot gas stream is too high, too much CO will be produced. In addition, the amount of O, OH and $O_2$ produced also will be excessive. It is essential that the total of these latter three constituents amount to less than about 0.2 volume percent of the total hot gas stream produced in gas generator assembly 12.

Typically, the hot gas stream will principally comprise from 10 to 50 vol % carbon monoxide, from about 6 to 40 vol % steam, and from about 10 to 40 vol % hydrogen along with a minor amount of $CO_2$. It is an advantage of the present invention that substantial amounts of carbon monoxide can be tolerated without any adverse effects on the acetylene production. This in turn permits the use of a hot gas stream formed by the combustion of a relatively inexpensive fuel and eliminates the necessity for a source of substantially pure hydrogen.

The hot gas stream enters interior zone 30 of reactant injector assembly 14. From the FIGURE it will be seen that coal injector tube 32 and the interior walls of reactant injector assembly 14 define an area of reduced cross-sectional flow area through which the hot gas must flow. This serves to accelerate the gas to a velocity of from about 500 to 4000 feet per second (150 to 1220 meters per second), and preferably to a velocity of from about 1000 to 2000 feet per second (300 to 610 meters per second). In addition, this configuration provides for the impingement of the hot gas upon a flowing stream of particulate coal introduced through passageway 34. The hot gas and coal impinge at an angle $\theta$ which nominally will be within the range of from about 15° to 50° and preferably about 30°. As depicted, the hot gas will impinge upon the entire periphery of the stream of coal flowing through passageway 34. It will be appreciated, however, that other configurations could be used such that the hot gas stream impinges upon the coal from a plurality of individual openings.

The coal entering through passageway 34 generally will be at ambient temperature. However, it also is within the scope of the invention that it be preheated so long as it is not heated to a temperture at which it will tend to cake or coke. It is essential to the present invention that the coal be in a fine particulate form. Thus, the coal must have a median particle size of less than about 100 microns, and preferably a median particle size of less than about 75 microns to ensure that adequate yields of acetylene will be formed.

In reaction chamber 16 the hot gas stream and particulate coal mix and react. It will be seen that reaction zone 36 diverges at an angle $\beta$ to provide an increasing cross-sectional flow area to decelerate the reaction mixture.

The angle $\beta$ must be less than about 7°, the reason for this being to avoid the possibility of any turbulence or backmixing which would alter the residence time within reaction zone 36 of some portion of the reaction mixture. However, the velocity of the stream of reaction mixture is reduced as quickly as possible to minimize heat losses. Thus the angle $\beta$ will preferably be about 5°. Preferably the velocity of the stream of reaction mixture will be reduced to from about 150 to 300 feet per second (46 to 92 meters per second). If the velocity gets too low the slag formed during the reaction will tend to stick to the walls of the reactor. Conversely, if the velocity is too high the length of the reactor must be greater to provide the same residence time with an attendant increase in thermal losses through the walls of the reactor. The length of reaction zone 36 and the velocity of the stream of reaction mixture flowing therethrough are selected such as to provide a residence time within reaction zone 36 within the range of from about 2 to 30 milliseconds, and preferably from about 5 to 10 milliseconds for optimum acetylene production.

The reaction mixture formed in reaction zone 36 then enters quench chamber 18 where it is contacted with a finely dispersed coolant medium which is introduced through openings 40 in quench zone 38. In quench zone 38 the reaction mixture is rapidly quenched in a time of from about 2 to 30 milliseconds, and preferably in a time of from about 2 to 10 milliseconds, to a temperature of less than 900° F. (750° K.) to prevent any destruction or degradation of the acetylene formed.

An illustration of the results which are obtainable in accordance with the present invention are set forth in the following example in which all percentages and parts referring to gases are by volume unless otherwise specified.

EXAMPLE

Using the apparatus substantially as depicted in the FIGURE a fuel, oxygen and steam are introduced into and reacted in gas generator assembly 12 to produce a hot gas stream having a temperature of 3610° F. (2260° K.). The hot gas stream has the following composition.

| Composition (Vol %) | |
|---|---|
| CO | 41.14 |
| $CO_2$ | 6.35 |
| $H^+$ | 0.28 |
| $H_2$ | 28.48 |
| $H_2O$ | 23.71 |
| $OH^-$ | 0.04 |

The hot gas stream passes into reactant injector assembly 14 and is accelerated to about 1000 feet per second (300 meters per second) as it is introduced into reaction chamber 16. Also introduced into reaction chamber 16, through reactant injector assembly 14, is a stream of Kentucky No. 9 coal which has the following analyses:

| PROXIMATE ANALYSIS | |
|---|---|
| Wt % Moisture | 1.61 |
| Wt % Ash | 8.53 |
| Wt % Volatiles | 41.06 |
| Wt % Fixed Carbon | 48.80 |

| ULTIMATE ANALYSIS | |
|---|---|
| Wt % Moisture | 1.61 |
| Wt % Carbon | 70.05 |
| Wt % Hydrogen | 4.92 |
| Wt % Nitrogen | 1.55 |
| Wt % Chlorine | 0.27 |
| Wt % Sulfur | 3.40 |
| Wt % Ash | 8.53 |
| Wt % Oxygen (by difference) | 9.67 |
| Higher Heating Value | |
| (Btu/lbm) | 13,000 |
| (Joules/gram) | 30,230 |

The coal is ground such that 80 wt % will pass through a 200 mesh screen (the coal has a median particle size of less than about 74 microns) and is introduced at a rate of 375 pounds per hour (47.3 grams per second).

In reaction chamber 16 the coal and hot gas impinge upon one another, the hot gas being introduced in an amount to provide 1.11 pounds of hot gas per pound of coal. The amount of coal and hot gas entering reaction chamber 16 are selected to provide a reaction temperature of 2390° F. (1580° K.). For convenience the reaction temperature is that measured just prior to the quench of reaction products of the hot gas and coal since, as it will be appreciated, the temperature is changing constantly throughout the reaction chamber. As depicted, the reaction chamber has an initial diverging section to provide an increasing cross-sectional flow area so that the hot gas-coal mixture is decelerated to a velocity of about 200 feet per second (61 meters per second). The pressure in the reaction chamber is about 32 psia (2.2 atm.) and the length of the reaction chamber and flow rates of hot gas and coal are selected such as to provide a residence time within the reaction chamber of about 7 milliseconds.

The reaction products entering quench chamber 18 are rapidly quenched with water which is introduced at the rate of 1.94 pounds per pound of coal. The water is finely atomized with gaseous nitrogen at a rate of 1.15 pounds of nitrogen per pound of coal to enhance the mixing of the quench stream with the products and provide for a rapid quench of the reaction products to a temperature of about 500° F. (530° K.).

The quenched reaction products are collected and analyzed. Gaseous reaction products are produced in an amount of 5.67 pounds per pound of coal with the following composition:

| | | |
|---|---|---|
| | $N_2$ | 15.28 |
| | $H_2$ | 13.22 |
| | $H_2O$ (by difference) | 45.68 |
| | CO | 15.86 |
| | $CO_2$ | 7.35 |
| | $CH_4$ | 1.11 |
| | $C_2H_2$ | 0.91 |
| | $C_2H_4$ | 0.22 |
| | Benzene | 0.36 |
| | Toluene | 0.01 |

In addition to the gaseous reaction products there also is produced 0.53 pounds of solids per pound of coal, principally comprising char, tar and soot. These also are collected, analyzed and found to have the following ultimate composition:

| | | |
|---|---|---|
| | Wt % Carbon | 75.47 |
| | Wt % Hydrogen | 1.69 |
| | Wt % Ash | 15.97 |
| | Wt % Others | 6.87 |

From the foregoing example it is determined that 42.47 wt % of the coal carbon is converted to the following products:

| | | |
|---|---|---|
| | Wt % to Carbon Monoxide and Carbon Dioxide | 16.78 |
| | Wt % to Methane | 5.11 |
| | Wt % to Acetylene | 8.33 |
| | Wt % to Ethylene | 1.99 |
| | Wt % to Benzene | 9.93 |
| | Wt % to Toluene | 0.33 |

From these results it is seen that the present invention provides for the direct production of acetylene from a readily available and abundant source of feed material such as coal. In addition, it will be appreciated that the present invention does not rely upon a large source of substantially pure hydrogen. Thus, while the yield of acetylene may not look as impressive as those obtainable in some other processes, such other processes generally require a far more valuable feedstock or the use of substantially pure hydrogen, or both, which add considerably to the cost of the acetylene produced. It also will be appreciated that the recovered solids (char) may be used as a source of fuel for producing additional hot gas for the treatment of coal, thus further enhancing the economics of the process.

From the foregoing, the principle, preferred construction and mode of operation of the invention have been illustrated and described as well as what is now considered to represent its best embodiment. It should be understood, however, that within the scope of the appended claims the invention may be practiced otherwise than as specifically illustrated and described.

What is claimed is:

1. A process for producing acetylene from coal comprising the sequential steps of:
   (a) introducing carbonaceous a fuel, oxygen and steam into a hot gas generation zone, the oxygen being introduced in an amount less than the stoichiometric amount required to react with all of the fuel;
   (b) reacting the fuel, oxygen and steam within the hot gas generation zone at a superatmospheric pressure and a temperature within the range of from about 3000° to 4500° F. (1920° to 2760° K.) to produce a hot gas stream principally comprising hydrogen, carbon monoxide and steam along with minor amounts of carbon dioxide, and controlling the temperature within said range such that the hot gas stream is essentially free of O, OH and $O_2$;
   (c) accelerating the hot gas stream to a velocity within the range of from about 500 to 4,000 feet per second (150 to 1220 meters per second) and introducing it into a coal reaction zone;
   (d) introducing a stream of particulate coal into said coal reaction zone, said coal being selected from the group consisting of bituminous and subbituminous coals, and having a median particle size of less than about 100 microns;
   (e) impinging said particulate coal and hot gas stream upon one another to cause intimate mixing and rapid reaction of said stream of particulate coal with said hot gas stream to form an entrained flow of particulate coal in said hot gas, decelerating said flow to a velocity of from about 150 to 300 ft/sec (46 to 92 meters per second), and controlling the amounts of said stream of particulate coal and said hot gas stream to produce in said reaction zone a pressure in the range of from about 10 to 100 psia (0.7 to 6.8 atm.) and a temperature of from about 1800° to 3000° F. (1260° to 1920° K.);
   (f) maintaining the mixture of coal and hot gas at said pressure and temperature for a time of from about 2 to 30 milliseconds to produce a product stream, said product stream including enhanced yields of acetylene along with other reaction products and char;
   (g) reducing the temperature of said product stream to less than about 900° F. (750° K.) in a time of less than about 2 milliseconds to substantially arrest any further reactions;

(h) separately recovering said acetylene and char; and
(i) utilizing said char as the source of at least a part of the fuel introduced into said hot gas generation zone.

2. The process of claim 1 wherein in step (b) said hot gas temperature is within the range of from about 3000° to 3500° F. (1920 to 2200° K.).

3. The process of claim 1 wherein in step (e) said reaction temperature is within the range of from about 2000° to 250° F. (1370° to 1640° K.).

4. The process of claim 1 wherein in step (b) said hot gas stream comprises from about 10–50 vol % CO, 6–40 vol % $H_2O$, and 10–40 vol % $H_2$.

5. The process of claim 1 wherein in step (e) said pressure is in the range of from about 14 to 20 psia (0.95 to 1.36 atm.).

6. The process of claim 1 wherein in step (f) the mixture of coal and hot gas are maintained at said pressure and temperature for a time of from about 5 to 10 milliseconds.

7. The process of claim 1 wherein in step (g) the temperature of said product stream is reduced to less than about 500° F. (530° K.).

8. The process of claim 1 wherein in step (e) said particulate coal and hot gas stream are impinged upon one another at an angle of about 30°.

9. The process of claim 1 wherein in step (e) said entrained flow of particulate coal and hot gas are decelerated to a velocity of about 200 feet per second (60 meters per second).

10. The process of claim 1 wherein said coal is a bituminous coal and has a median particle size of less than about 75 microns.

11. A process for producing acetylene from coal comprising the sequential steps of:
 (a) introducing carbonaceous a fuel, oxygen and steam into a hot gas generation zone, the oxygen being introduced in an amount less than the stoichiometric amount required to react with all of the fuel;
 (b) reacting the fuel, oxygen and steam within the hot gas generation zone at a superatmospheric pressure and a temperature within the range of from about 3000° to 4500° F. (1920° to 2760° K.) to produce a hot gas stream principally comprising hydrogen, carbon monoxide and steam along with minor amounts of carbon dioxide, and controlling the temperature within said range such that the hot gas stream is essentially free of O, OH and $O_2$;
 (c) accelerating the hot gas stream to a velocity within the range of from about 500 to 4,000 feet per second (150 to 1220 meters per second) and introducing it into a coal reaction zone;
 (d) introducing a stream of a particulate bituminous coal into said reaction zone, said coal having a median particle size of less than about 75 microns;
 (e) impinging said particulate coal and hot gas stream upon one another at an angle of from 15° to 50° to cause intimate mixing and reaction of said stream of particulate coal with said hot gas stream to form an entrained flow of particulate coal in said hot gas, decelerating said flow to a velocity of from about 150 to 300 ft/sec (46 to 92 meters per second), and controlling the amounts of said stream of particulate coal and said hot gas stream to produce in said reaction zone a pressure in the range of from about 10 to 100 psia (0.7 to 6.8 atm) and a temperature of from about 1800° to 3000° F. (1260° to 1920° K.);
 (f) maintaining the mixture of coal and hot gas at said pressure and temperature for a time of from about 2 to 30 milliseconds to produce a product stream entrained in said hot gas, said product stream including enhanced yields of acetylene along with other reaction products and char;
 (g) reducing the temperature of said product stream to less than about 900° F. (750° K.) in a time of less than about 2 milliseconds to substantially arrest any further reactions;
 (h) separately recovering said acetylene and char; and
 (i) utilizing said char as the source of at least a part of the fuel introduced into said hot gas generation zone.

12. The process of claim 11 wherein in step (b) said hot gas temperature is within the range of from about 3000° to 3500° F. (1920° to 2200° K.).

13. The process of claim 11 wherein in step (e) said reaction temperature is within the range of from about 2000° to 2500° F. (1370° to 1640° K.).

14. The process of claim 11 wherein in step (b) said hot gas stream comprises from about 10–50 vol % CO, 6–40 vol % $H_2O$, and 10–40 vol % $H_2$.

15. The process of claim 11 wherein in step (e) said pressure is in the range of from about 14 to 20 psia (0.95 to 1.36 atm).

16. The process of claim 11 wherein in step (f) the mixture of coal and hot gas are maintained at said pressure and temperature for a time of from about 5 to 10 milliseconds.

17. The process of claim 11 wherein in step (g) the temperature of said product stream is reduced to less than about 500° F. (530° K.).

18. The process of claim 11 wherein in step (e) said particulate coal and hot gas stream are impinged upon one another at an angle of about 30°.

19. The process of claim 11 wherein in step (e) said entrained flow of particulate coal and hot gas are decelerated to a velocity of about 200 feet per second (60 meters per second).

20. A process for producing acetylene from coal comprising the sequential steps of:
 (a) introducing carbonaceous a fuel, oxygen and steam into a hot gas generation zone, the oxygen being introduced in an amount less than the stoichiometric amount required to react with all of the fuel;
 (b) reacting the fuel, oxygen and steam within the hot gas generation zone at a superatmospheric pressure and a temperature within the range of from about 3000° to 4500° F. (1920° to 2760° K.) to produce a hot gas stream principally comprising 10–40 vol % hydrogen, 10–50 vol % carbon monoxide and 6–40 vol % steam along with minor amounts of carbon dioxide, and oontrolling the temperature within said range such that the hot gas stream is essentially free of O, OH and $O_2$;
 (c) accelerating the hot gas stream to a velocity within the range of from about 500 to 4,000 feet per second (150 to 1220 meters per second) and introducing it into a coal reaction zone;
 (d) introducing a stream of particulate bituminous coal at ambient temperature into said coal reaction zone, said coal having a median particle size of less than about 100 microns;
 (e) impinging said particulate coal and hot gas stream upon one another at an angle of from 15° to 50° to cause intimate mixing and reaction of said stream of particulate coal with said hot gas stream to form an entrained flow of particulate coal in said hot gas, decelerating said flow to a velocity of from about 150 to 300 ft/sec (46 to 92 meters per second), and controlling the amounts of said stream of particulate coal and said hot gas stream to produce in said reaction zone a pressure in the range of from about 14 to 20 psia (0.95 to 1.36 atm) and a temperature of from about 1800° to 3000° F. (1260° to 1920° K.);

(f) maintaining the mixture of coal and hot gas at said pressure and temperature for a time of from about 5 to 10 milliseconds to produce a product stream entrained in said hot gas, said product stream including enhanced yields of acetylene along with other reaction products and char;

(g) reducing the temperature of said product stream to less than about 500° F. (530° K.) in a time of less than about 2 milliseconds to substantially arrest any further reactions;

(h) separately recovering said acetylene and char; and (i) utilizing said char as the source of at least a part of the fuel introduced into said hot gas generation zone.

21. The process of claim 20 wherein in step (b) said hot gas temperature is within the range of from about 3000° to 3500° F. (1920° to 2200° K.).

22. The process of claim 21 wherein in step (e) said reaction temperature is within the range of from about 2000° to 2500° F. (1370° to 1640° K.).

23. The process of claim 22 wherein in step (e) said particulate coal and hot gas stream are impinged upon one another at an angle of about 30°.

24. The proces of claim 23 wherein in step (e) said entrained flow of particulate coal and hot gas are decelerated to a velocity of about 200 feet per second (60 meters per second).

25. The process of claim 24 wherein said coal has a median particle size of less than about 75 microns.

* * * * *

UNITED STATES PATENT AND TRADEMARK OFFICE
CERTIFICATE OF CORRECTION

PATENT NO. : 4,536,603

DATED : August 20, 1985

INVENTOR(S) : Kenneth M. Sprouse et al

It is certified that error appears in the above-identified patent and that said Letters Patent is hereby corrected as shown below:

```
Column 8, line 23, delete "carbonaceous a" and insert --a carbonaceous--.
Column 9, line 10, delete " 250°" and insert --2500°--;
          line 36, delete "carbonaceous a" and insert --a carbonaceous--.
Column 10,line 43, delete "carbonaceous a" and insert --a carbonaceous--.
```

Signed and Sealed this

Twelfth Day of November 1985

[SEAL]

Attest:

Attesting Officer

DONALD J. QUIGG

Commissioner of Patents and Trademarks